(12) United States Patent
Purcell Ngambo

(10) Patent No.: US 9,498,529 B2
(45) Date of Patent: Nov. 22, 2016

(54) METHODS FOR TREATING OR PREVENTING INFLUENZA VIRUS INFECTION BY ADMINISTERING A SERINE PROTEASE INHIBITOR

(71) Applicant: REGENERON PHARMACEUTICALS, INC., Tarrytown, NY (US)

(72) Inventor: Lisa A. Purcell Ngambo, Garnerville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 13/862,497

(22) Filed: Apr. 15, 2013

(65) Prior Publication Data

US 2013/0273070 A1   Oct. 17, 2013

Related U.S. Application Data

(60) Provisional application No. 61/624,519, filed on Apr. 16, 2012, provisional application No. 61/759,469, filed on Feb. 1, 2013.

(51) Int. Cl.
| | | |
|---|---|---|
| *A61K 45/06* | (2006.01) | |
| *A61K 39/395* | (2006.01) | |
| *A61K 39/145* | (2006.01) | |
| *A61K 39/42* | (2006.01) | |
| *C07K 16/40* | (2006.01) | |
| *A61K 39/00* | (2006.01) | |

(52) U.S. Cl.
CPC ......... *A61K 39/3955* (2013.01); *A61K 39/145* (2013.01); *A61K 39/42* (2013.01); *A61K 45/06* (2013.01); *C07K 16/40* (2013.01); *A61K 2039/505* (2013.01)

(58) Field of Classification Search
None
See application file for complete search history.

(56) References Cited

U.S. PATENT DOCUMENTS 6,166,194 A * 12/2000 Wong et al. ............... 536/23.5

FOREIGN PATENT DOCUMENTS

| JP | 2008 247864 | 10/2008 |
|---|---|---|
| JP | 2008 308438 | 12/2008 |
| WO | 2004/097358 | 11/2004 |
| WO | 2010/149549 | 12/2010 |

OTHER PUBLICATIONS

Bottcher-Friebertshauser et al. (Journal of Virology, Feb. 2011, vol. 85, p. 1554-1562).*
Weltzin et al. (Clinical Microbiology Reviews, 1999, p. 383-393).*
Bahgat et al., "Inhibition of lung serine proteases in mice: a potentially new approach to control" Virology Journal (Jan. 20, 2011) 8(1):27.
Bertram et al., "Novel Insights into proteolytic cleavabe of influenza virus hemagglutinin" Rev. Med. Virol. (2010) 20:298-310.
Bottcher et al., "Proteolytic Activation of Influenza Viruses by Serine Proteases TMPRSS2 and HAT from Human Airway Epithelium" Journal of Virology (Oct. 2006) 80(19):9896-9898.
Bottcher et al., "MDCK cells that express proteases TMPRSS2 and HAT provide a cell system to propagate influenza viruses in the absence of trypsin and to study cleavage of HA and its inhibition." Vaccine (Oct. 23, 2009) 27(45):6324-6329.
Botcher-Friebertshauser et al., "Cleavage of Influenza Virus Hemagglutinin by Airway Proteases TMPRSS2 and HAT Differs in Subcellular Localization and Susceptibility fo Protease Inhibitors" Journal of Virology (Jun. 2010) 84(1):5605-5614.
Botcher-Friebertshauser et al., "Inhibition of Influenza Virus Infection in Human Airway Cell Cultures by an Antisense Peptide-Conjugated Morpholino Oligomer Targeting the Hemagglutinin-Activating Protease TMPRSS2" Journal of Virology (Feb. 15, 2011) 85(4):1554-1562.
Botcher-Friebertshauser et al., "Hemagglutinin activating host cell proteases provide promising drug targets for the treatment of influenza A and B virus infections" Vaccine (Dec. 2012) 30(51):7374-7390.
Govorkova et al., "Combination Chemotherapy for Influenza" Viruses (2010) 2:1510-1529.
Hoopes et al., "Triple combination antiviral drug (TCAD) composed of amantadine, oseltamivir, and ribavirin impedes the selection of drug-resistant influenza A virus." PLoS One (Dec. 2011) 6(12):e29778.
Kido et al., "Role of host cellular proteases in the pathogenesis of influenza and influenza-induced multiple organ failure" Biochim Biophys Acta. (Jan. 2012)1824(1):186-94.
Szabo et al., "Type II transmembrane serine proteases in development and disease" International Journal of Biochemistry and Cell Biology (Jun. 1, 2008) 40(6-7)1297-1315.
Nguyen J. et al., Triple Combination of Oseltamivir, Amantadine, and Ribavirin Displays Synergistic Activity Against Multiple Influenza Virus Strains In Vitro. Antimicrob Agents Chemother. Oct. 2009; vol. 53, No. 10, pp. 4115-4126.

\* cited by examiner

*Primary Examiner* — Agnieszka Boesen
(74) *Attorney, Agent, or Firm* — Veronica Mallon; Frank Cottingham; Karl Bozicevic

(57) ABSTRACT

The present invention provides methods for treating or preventing influenza virus infection. The methods of the present invention comprise administering to a subject in need thereof a pharmaceutical composition comprising a type II transmembrane serine protease (TTSP) inhibitor. The TTSP inhibitor preferably functions by inhibiting the proteolytic cleavage of influenza hemagglutinin (HA0) into the functional subunits HA1 and HA2. In certain embodiments, the TTSP inhibitor is an inhibitor of transmembrane protease serine S1 member 2 (TMPRSS2), such as an anti-TMPRSS2 antibody or antigen-binding fragment thereof.

4 Claims, 16 Drawing Sheets

METHODS FOR TREATING OR PREVENTING INFLUENZA VIRUS INFECTION BY ADMINISTERING A SERINE PROTEASE INHIBITOR

CROSS-REFERENCE TO RELATED APPLICATIONS

This application claims the benefit under 35 U.S.C. §119 (e) of U.S. provisional application Nos. 61/624,519, filed on Apr. 16, 2012; and 61/759,469, filed on Feb. 1, 2013, the disclosures of which are herein incorporated by reference in their entireties.

FIELD OF THE INVENTION

The present invention relates to the treatment and prophylaxis of influenza virus infection. More specifically, the invention relates to the use of type II transmembrane serine protease inhibitors (TTSPs), such as anti-TMPRSS2 antibodies, to treat or prevent influenza virus infection in a subject.

BACKGROUND

The influenza virus infection process is initiated by the attachment of virus particles (virions) to target cells followed by fusion of the viral envelope with the target cell membrane. Viral attachment and cell fusion are mediated by the viral envelope protein hemagglutinin (HA). HA consists of two subunits: HA1 which mediates the attachment step, and HA2 which mediates the fusion step. HA is initially synthesized as an inactive precursor (HA0) in which HA1 and HA2 are connected by a protease-sensitive linker sequence. Cleavage of the linker by host cell proteases produces the functional HA1 and HA2 subunits. Since cleavage of HA is an essential, host-mediated step in the influenza virus infection process, host cell proteases that mediate the activation of HA have been proposed as therapeutic targets against influenza infection. (See, e.g., Bottcher et al., (2006) *J. Virol.* 80:9896-9898).

Host cell proteases that have been implicated in the cleavage of influenza HA include TTSPs such as transmembrane protease serine S1 member 2 (TMPRSS2), TMPRSS4 and human airway trypsin-like protease (HAT). (See, e.g., Bahgat et al., (2011) *Virol. J.* 8:27, and references cited therein). These proteases are expressed in human airway epithelial cells. (See Bertram et al., (2010) *Rev. Med. Virol.* 20:298-310). It has been reported that treatment of a human airway epithelial cell line (Calu-3) with a single-stranded DNA-like antisense agent (PPMO) that sterically blocked TMPRSS2 cRNA caused a reduction in H1N1 viral titers in vitro. (See Bottcher-Friebertshauser et al., (2011) *J. Virol.* 85:1554-1562). Nevertheless, a protective effect of TTSP attenuation (e.g., TMPRSS2 knock-out) in an animal model has not been directly demonstrated. In addition, the use of therapeutic agents that target the proteolytic activity of a TTSP (e.g., an anti-TMPRSS2 antibody) in the treatment and/or prevention of influenza virus infection has not been shown. Accordingly, there exists a need in the art for novel, highly effective therapeutic approaches against influenza, which take advantage of the role of host cell proteases in the infection process.

BRIEF SUMMARY OF THE INVENTION

The present invention addresses the aforementioned need in the art by providing methods for treating or preventing influenza virus infection. The methods of the present invention comprise administering to a subject in need thereof a pharmaceutical composition comprising a type II transmembrane serine protease (TTSP) inhibitor. In certain embodiments, the TTSP is an inhibitor of TMPRSS2. Exemplary TMPRSS2 inhibitors that can be used in the context of the present invention include, e.g., small molecule protease inhibitors, peptide inhibitors, nucleic acid-based inhibitors, and antibodies or antigen-binding fragments of antibodies that specifically bind TMPRSS2.

According to certain aspects of the present invention, a TMPRSS2 inhibitor is administered to a subject in need thereof, wherein the TMPRSS2 inhibitor is specific for TMPRSS2 and/or is the only TTSP inhibitor administered to the subject. For example, in certain embodiments, an anti-TMPRSS2 antibody is administered to a subject, wherein the anti-TMPRSS2 antibody only inhibits the activity of TMPRSS2, and no other TTSP inhibitor (e.g., TMPRSS4 inhibitor, HAT inhibitor, etc.) is administered to the subject.

The present invention also includes embodiments wherein a second therapeutic agent is administered to the subject in combination with the TTSP inhibitor. For example, the present invention includes methods in which an anti-TMPRSS2 antibody is administered to a subject in combination with one or more antiviral agents, and/or in combination with an anti-influenza antibody.

Other embodiments of the present invention will become apparent from a review of the ensuing detailed description.

DETAILED DESCRIPTION

Figure 1:
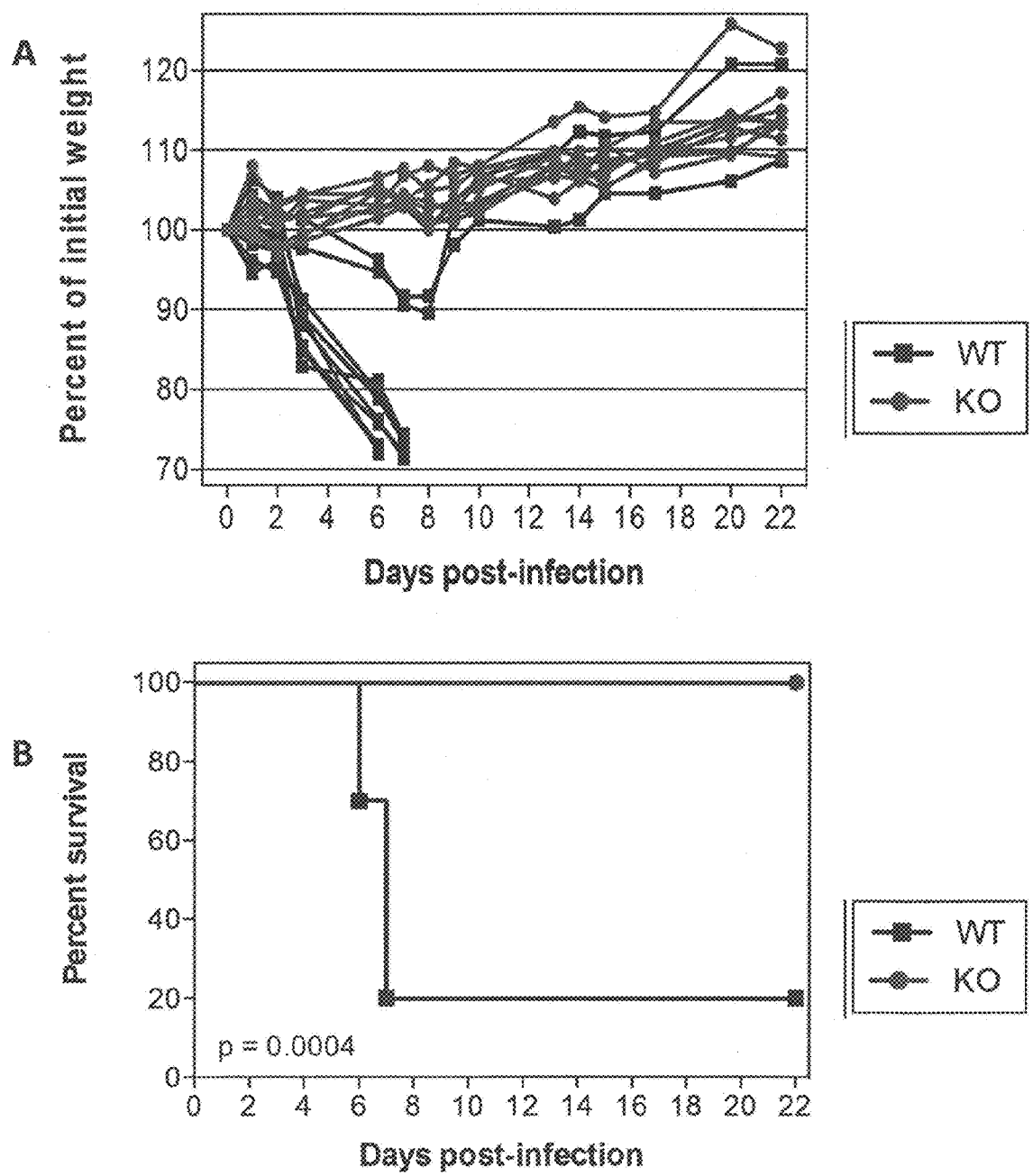
FIGS. 1-4 depict the results of four different trials (Trials 1-4, respectively) in which wild-type mice ("WT," closed squares) and TMPRSS2 knock out mice ("KO," closed circles) were challenged with 750 PFUs of H1N1 influenza virus and assessed for percent weight change (panel A) and percent survival (panel B) at several time points after infection.
Figure 2:
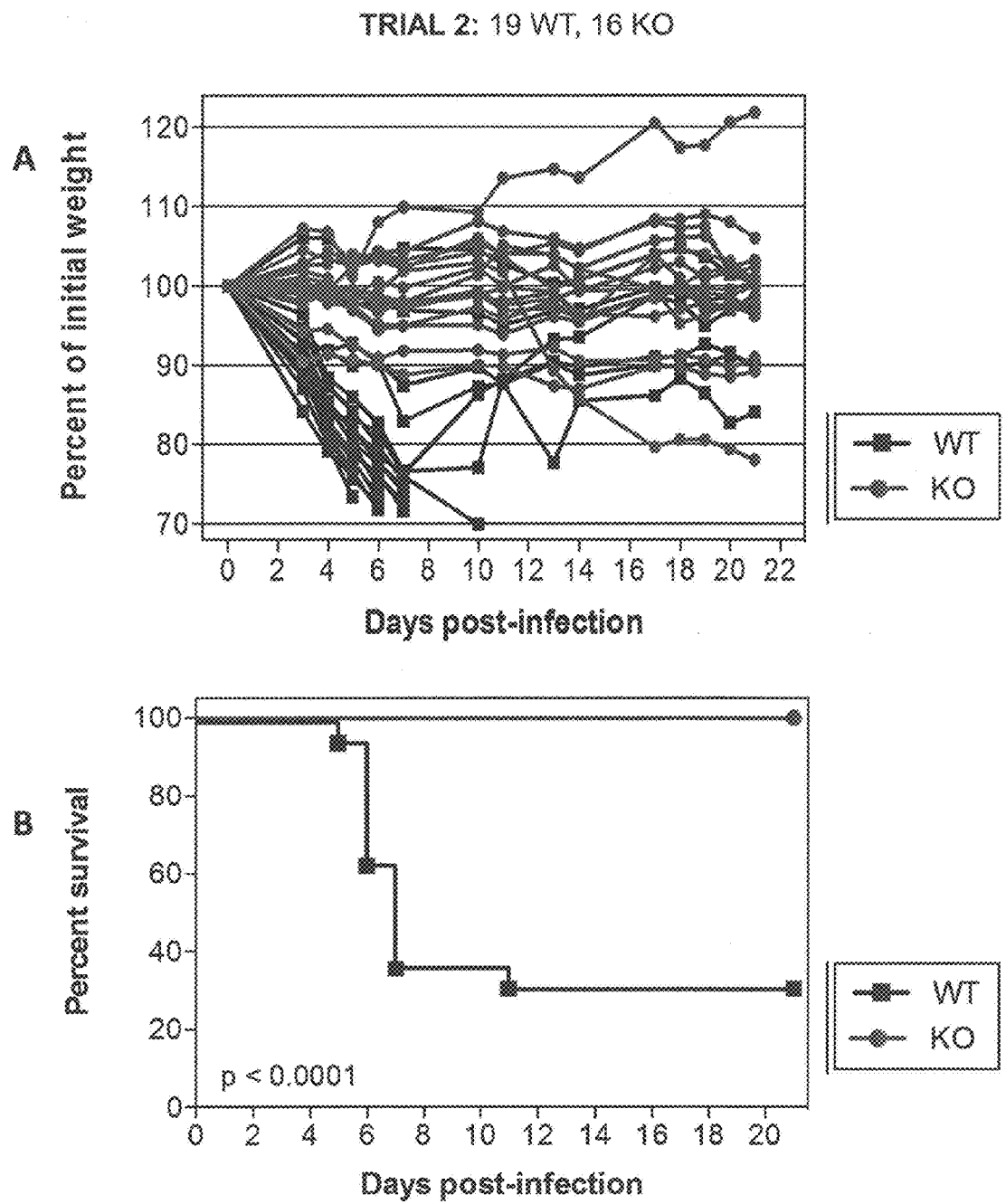
Figure 3:
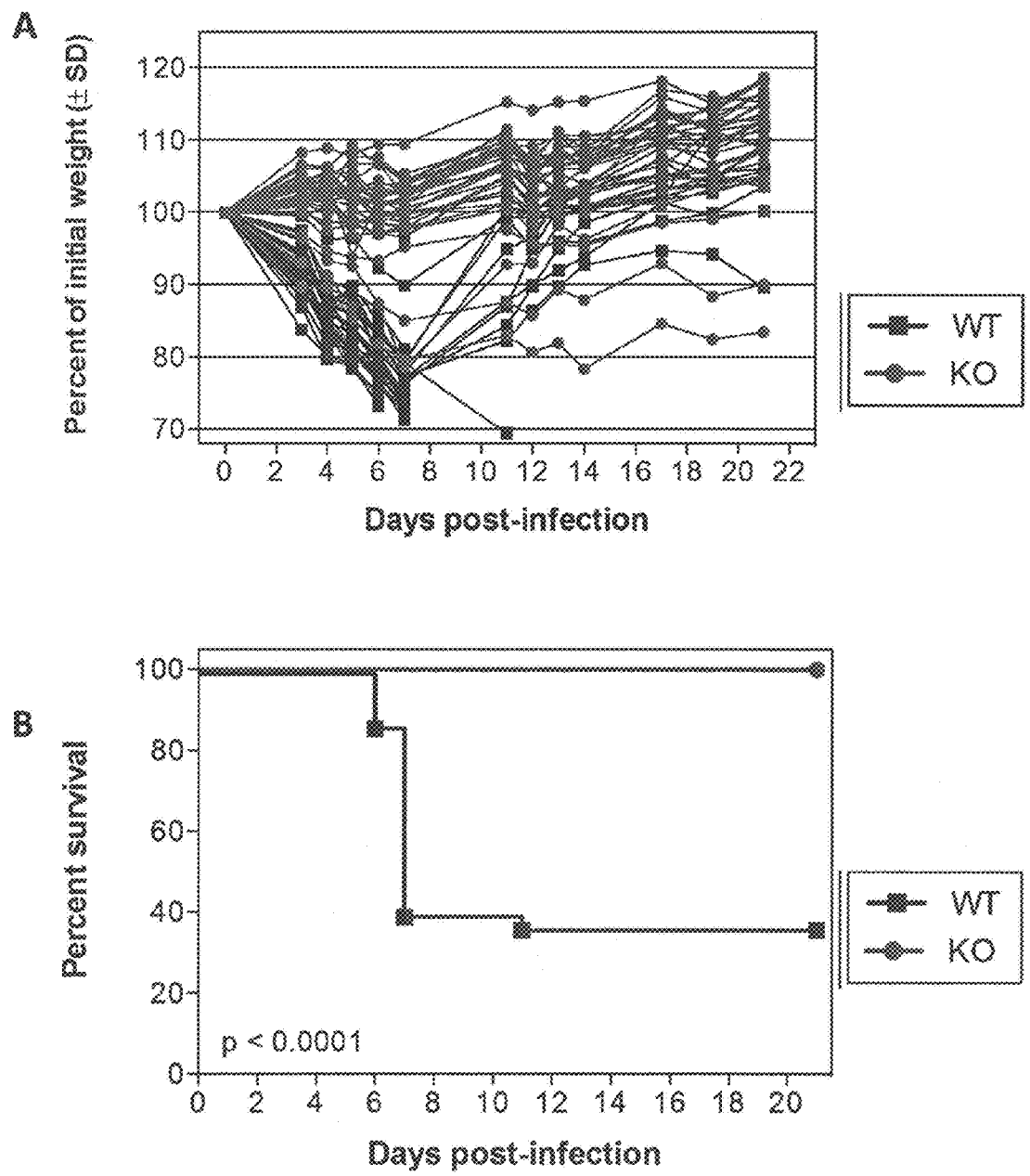
Figure 4:
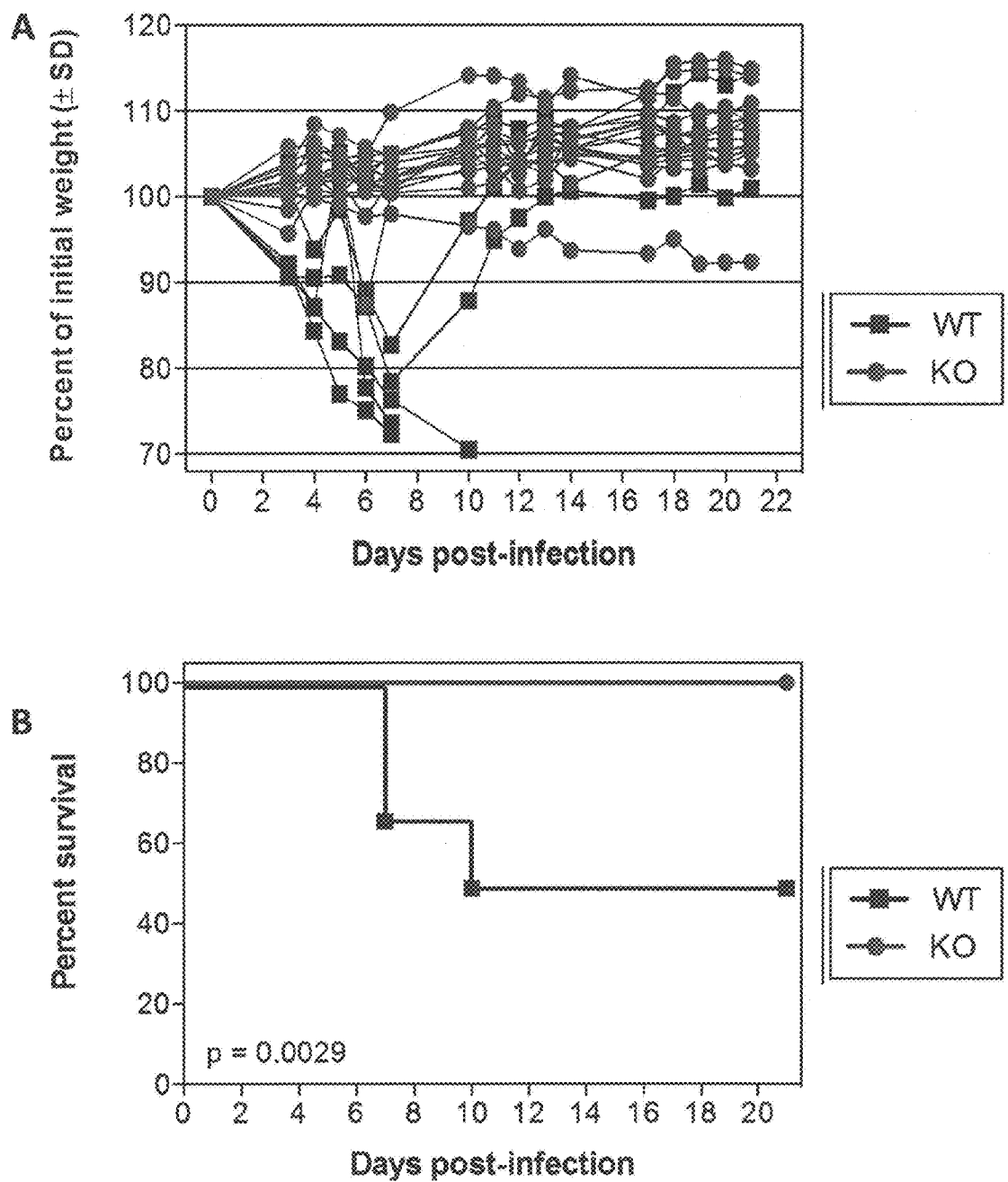

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating or Preventing Influenza Virus Infection

The present invention provides methods for treating or preventing influenza virus infection. As used herein, the expression "treating influenza virus infection" means improving, reducing, or alleviating at least one symptom or biological consequence of influenza virus infection in a mammal, and/or reducing or decreasing influenza virus titer, load, replication or proliferation in a mammal following exposure to an influenza virus. The expression "treating influenza virus infection" also includes shortening the time period during which a subject exhibits at least one symptom or biological consequence of influenza virus infection after being infected by influenza virus. Methods for treating influenza virus infection, according to the present invention, comprise administering a pharmaceutical composition of the present invention to a subject after the subject is infected with an influenza virus and/or after the subject exhibits or is diagnosed with one or more symptoms or biological consequences of influenza virus infection.

As used herein, the expression "preventing influenza virus infection" means preventing at least one symptom or biological consequence of influenza virus infection in a mammal, and/or inhibiting or attenuating the extent to which influenza virus is capable of entering, spreading, and/or propagating within/among cells of an animal body. The expression "preventing influenza virus infection" also includes decreasing the susceptibility of a subject to at least one symptom or biological consequence of influenza virus infection. Methods for preventing influenza virus infection (i.e., prophylaxis) comprise administering a pharmaceutical composition of the present invention to a subject before the subject is infected with an influenza virus and/or before the subject exhibits one or more symptoms or biological consequences of influenza virus infection. Methods for preventing influenza virus infection may include administering a pharmaceutical composition of the present invention to a subject at a particular time period or season of the year (e.g., during the 1-2 month period just prior to the time at which peak numbers of individuals are typically found to experience influenza virus infection), or before the subject travels to or is exposed to an environment with high frequencies of influenza virus infection, and/or before the subject is exposed to other subjects who are infected with influenza virus.

The expression "symptom or biological consequence of influenza virus infection," as used herein includes one or more of nasal congestion, sinus congestion, runny nose, sneezing, body (muscle) ache, head ache, chills, fever, cough, sore throat, fatigue, ear ache, or a diagnostic indicator of influenza virus infection. Diagnostic indicators of influenza virus infection include, e.g., detection of influenza by viral culture, hemagglutinin agglutination inhibition (HAI) assay, immunofluorescence, or nucleic acid-based detection (e.g., RT-PCR) using an appropriate specimen (e.g., nasal swab, nasopharyngeal swab, throat swab, endotracheal aspirate, sputum, bronchial wash, etc.). Thus, a subject who tests positive for influenza virus infection by a diagnostic assay is considered a subject exhibiting a "symptom or biological consequence of influenza virus infection."

The experiments described herein show, inter alia, that animals that do not express a functional type II transmembrane serine protease (e.g., TMPRSS2) do not exhibit a significant increase in certain influenza-infected cell types in the lungs following influenza virus challenge. In particular, TMPRSS2 knock-out mice that were challenged with influenza virus did not show an increase in influenza-positive alveolar macrophages, neutrophils or epithelial cells in the lungs, whereas the frequency of these influenza-infected cell types was significantly increase in the lungs of wild-type mice after influenza virus challenge. TMPRSS2 knock-out mice also exhibited complete survival and weight gain/maintenance characteristics following influenza virus challenge. Accordingly, the present invention also provides methods for preventing or reducing the accumulation of influenza-infected alveolar macrophages, influenza-infected neutrophils and/or influenza-infected epithelial cells in the lungs of a subject that has been exposed to or challenged with influenza virus, wherein the method comprises administering to the subject a pharmaceutical composition comprising a type II transmembrane serine protease (TTSP) inhibitor.

Patient Population

The methods of the present invention can be used to treat or prevent influenza virus infection in any subject for whom such treatment or prevention would be beneficial. The subject can be a human or non-human animal (e.g., equine, canine, bovine, feline, ovine, porcine, avian, etc.). With regard to methods of treatment, the subject to be treated includes any individual who exhibits at least one symptom or biological consequence of influenza virus infection (as that phrase is defined herein). With regard to methods of prevention, the subject can be any individual who may be at risk of being exposed to influenza virus or who has the potential of coming into contact with another individual who is infected by influenza virus.

In either the "treatment" or "prevention" context, the methods of the present invention may be particularly useful for treating or preventing influenza virus infection in a patient group selected from elderly subjects, cancer patients (e.g., individuals undergoing chemotherapy, radiation or other anti-cancer therapeutic regimen), and immuno-incompetent or immunocompromised individuals. For example, subjects who are unable to adequately respond to influenza vaccination or other antiviral therapies, or who are intolerant to conventional therapies (e.g., individuals with egg allergies who are precluded from influenza vaccination), are subjects for whom the methods of the present invention may be of therapeutic or prophylactic benefit.

TTSP Inhibitors

The methods of the present invention comprise administering a pharmaceutical composition comprising a type II transmembrane serine protease (TTSP) inhibitor to a subject. Exemplary TTSPs include transmembrane protease serine S1 member 2 (TMPRSS2), transmembrane protease serine S1 member 4 (TMPRSS4), and human airway trypsin-like protease (HAT). The TTSP inhibitor can be a small molecule protease inhibitor, a nucleic acid-based inhibitor (e.g., siRNA, ribozyme, antisense construct, etc.), antigen-binding protein (e.g., antibody or antigen-binding fragment thereof), or a blocking peptide/peptide inhibitor. The TTSP inhibitor may function by inhibiting or reducing the ability of a TTSP to proteolytically cleave hemagglutinin precursor protein (HA0) into the HA1 and HA2 subunits.

In certain exemplary embodiments, the TTSP inhibitor is a TMPRSS2 inhibitor such as an antibody or antigen-binding fragment thereof that specifically binds TMPRSS2 and inhibits the proteolytic activity of TMPRSS2. For example, the antibody or antigen-binding fragment thereof may inhibit or reduce the ability of TMPRSS2 to proteolytically cleave hemagglutinin precursor protein (HA0) into the HA1 and HA2 subunits. An antibody is deemed to inhibit the protease activity of a TTSP (e.g., TMPRSS2) if the antibody, when mixed with the TTSP, reduces the proteolytic activity of the TTSP by at least 25% (e.g., 30%, 40%, 50%, 60%, 70%, 80%, 90% or 100%) relative to a non-inhibitory control molecule tested under identical or substantially identical experimental conditions.

In certain embodiments of the present invention, the TTSP inhibitor is an anti-TMPRSS2 antibody or antigen-binding fragment thereof that inhibits the protease activity of TMPRSS2 but does not substantially inhibit the protease activity of any other TTSP. For purposes of the present disclosure, an anti-TMPRSS2 antibody does not "substantially inhibit the protease activity of any other TTSP" if the antibody, when mixed with TMPRSS4 or HAT, has no effect on the proteolytic activity of TMPRSS4 or HAT, or reduces the proteolytic activity of TMPRSS4 or HAT by no more than 25% (e.g., by 20%, 15%, 10%, 5%, or less) relative to a non-inhibitory control molecule tested under identical or substantially identical experimental conditions.

In certain embodiments wherein the TTSP inhibitor is a TMPRSS2 inhibitor, the TMPRSS2 inhibitor is the only TTSP inhibitor administered to the subject. Thus, in the context of such embodiments of the invention, the administration of any other TTSP inhibitor (e.g., a TMPRSS4 inhibitor or a HAT inhibitor) besides an anti-TMPRSS2 inhibitor is specifically excluded.

Antibodies and Antigen-Binding Fragments of Antibodies

As indicated above, the TTSP inhibitor used in the context of the methods of the present invention (e.g., a TMPRSS2 inhibitor) can be an antibody or antigen-binding fragment thereof (e.g., an antibody or antigen-binding fragment thereof that specifically binds TMPRSS2). The term "antibody", as used herein, means any antigen-binding molecule or molecular complex comprising at least one complementarity determining region (CDR) that specifically binds to or interacts with a particular antigen (e.g., TMPRSS2). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-TMPRSS2 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al., *Nucl. Acids Res.* 20:6287-6295 (1992)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four-chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

Pharmaceutical Compositions and Methods of Administration

The present invention includes methods which comprise administering a TTSP inhibitor (e.g., an anti-TMPRSS2 antibody) to a subject, wherein the TTSP inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of TTSP inhibitor (e.g., anti-TMPRSS2 antibody) administered to a subject according to the methods of the present invention is, generally, a therapeutically effective amount. As used herein, the phrase "therapeutically effective amount" means a dose of TTSP inhibitor that results in a detectable improvement in one or more symptoms or biological consequences of influenza virus infection, as that expression is defined herein. As will be appreciated by persons of ordinary skill in the art, various animal models can be used to establish whether a particular amount of a candidate TTSP inhibitor is a therapeutically effective amount. A "therapeutically effective amount" of a TTSP inhibitor also includes a quantity of TTSP inhibitor (e.g., anti-TMPRSS2 antibody) that is able to reduce the proteolytic activity of the TTSP (e.g., the ability to cleave HA0 into HA1 and HA2 subunits) by at least 25% relative to a non-inhibitor control molecule tested under identical or substantially identical experimental conditions.

In the case of an anti-TMPRSS2 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-TMPRSS2 antibody.

The amount of anti-TMPRSS2 antibody contained within the individual doses may be expressed in terms of milligrams of antibody per kilogram of patient body weight (i.e., mg/kg). For example, the anti-TMPRSS2 antibody may be administered to a patient at a dose of about 0.0001 to about 10 mg/kg of patient body weight.

Combination Therapies

The methods of the present invention, according to certain embodiments, may comprise administering a pharmaceutical composition comprising a TTSP inhibitor (e.g., an anti-TMPRSS2 antibody) to a subject in combination with a second therapeutic agent. The phrase "in combination with a second therapeutic agent" means that the second therapeutic agent is administered to the subject before (e.g., about 1 to 72 hours prior to), after (e.g., about 1 to 72 hours following), or concurrent with (e.g., within about 1 hour of) administration of the pharmaceutical composition comprising the TTSP inhibitor to the subject.

The second therapeutic agent can be any therapeutic agent that is useful for the treatment or prevention of influenza virus infection on its own. Non-limiting examples of second therapeutic agents that may be administered in combination with a pharmaceutical composition comprising a TTSP inhibitor include, e.g., amantadine, rimantadine, oseltamivir, zanamivir, aprotinin, leupeptin, cationic steroid antimicrobials (see, e.g., US 2007/0191322), an influenza vaccine (e.g., killed, live, attenuated whole virus or subunit vaccine), or an antibody against influenza virus (e.g., an anti-hemagglutinin antibody).

Administration Regimens

According to certain embodiments of the present invention, multiple doses of a pharmaceutical composition comprising a TTSP inhibitor (e.g., anti-TMPRSS2 antibody) may be administered to a subject over a defined time course. The methods according to this aspect of the invention comprise sequentially administering to a subject multiple doses of a TTSP inhibitor. As used herein, "sequentially administering" means that each dose of TTSP inhibitor is administered to the subject at a different point in time, e.g., on different days separated by a predetermined interval (e.g., hours, days, weeks or months). The present invention includes methods which comprise sequentially administering to the patient a single initial dose of a TTSP inhibitor, followed by one or more secondary doses of the TTSP inhibitor, and optionally followed by one or more tertiary doses of the TTSP inhibitor.

The terms "initial dose," "secondary doses," and "tertiary doses," refer to the temporal sequence of administration of the TTSP inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of TTSP inhibitor, but will generally differ from one another in terms of frequency of administration. In certain embodiments, however, the amount of TTSP inhibitor contained in the initial, secondary and/or tertiary doses will vary from one another (e.g., adjusted up or down as appropriate) during the course of treatment.

In one exemplary embodiment of the present invention, each secondary and/or tertiary dose is administered 1 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) days after the immediately preceding dose. The phrase "the immediately preceding dose," as used herein, means, in a sequence of multiple administrations, the dose of TTSP inhibitor which is administered to a patient prior to the administration of the very next dose in the sequence with no intervening doses.

The methods according to this aspect of the invention may comprise administering to a patient any number of secondary and/or tertiary doses of a TTSP inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 29 days after the immediately preceding dose. Similarly, in embodiments involving multiple tertiary doses, each tertiary dose may be administered at the same frequency as the other tertiary doses. For example, each tertiary dose may be administered to the patient 1 to 60 days after the immediately preceding dose. Alternatively, the frequency at which the secondary and/or tertiary doses are administered to a patient can vary over the course of the treatment regimen. The frequency of administration may also be adjusted during the course of treatment by a physician or health care provider depending on the needs of the individual patient following clinical examination.

Any of the foregoing administration regiments may include the administration of one or more additional therapeutic agents in combination with the TTSP inhibitor, as defined elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

TMPRSS2 Knock-Out Mice Exhibit Improved Survival And Weight Maintenance Compared to Wild-Type Mice Following Influenza A Virus Infection Initial experiments were conducted using engineered knock-out mice which fail to express a functional TMPRSS2 protein ("TMPRSS2-KO"). Wild-type littermate mice ("WT") were used as controls. Four separate trials (Trial 1-Trial 4) were carried out in which TMPRSS2-KO mice and WT controls were infected with 10×MLD$_{50}$ (750 PFUs) of A/Puerto Rico/8/1934 H1N1 virus intranasally. Mice were weighed approximately each day after infection and monitored for survival. Euthanasia of infected mice occurred when the animals lost 25% or more of the initial body weight as determined at the time of infection (e.g., day 0). Mice were also monitored for other overt signs of morbidity, including hunched posture, piloerection, and/or neurological symptoms such as hind-limb paralysis. Results of Trials 1-4 are shown in FIGS. 1-4, respectively. Survival data from the individual Trials is summarized in Table 1.

TABLE 1

| Summary of Influenza Infection Trials | | | | | | | | |
|---|---|---|---|---|---|---|---|---|
| | TRIAL 1 | | TRIAL 2 | | TRIAL 3 | | TRIAL 4 | |
| | WT | KO | WO | KO | WT | KO | WT | KO |
| # Mice | 10 | 10 | 19 | 16 | 30 | 32 | 6 | 15 |
| % Survival | 20 | 100 | 31 | 100 | 36 | 100 | 50 | 100 |

As shown in FIGS. 1-4, most of the infected TMPRSS2-KO mice exhibited normal weight gain/maintenance for at least 21 days following infection. The majority of infected WT mice, by contrast, exhibited dramatic and rapid weight loss by as early as day 3 post-infection, which is an indicative response to experimental influenza infection in mice.

Moreover, in all four Trials TMPRSS2-KO mice exhibited 100% survival throughout the entire experimental period compared with 20-50% survival for the WT mice.

This Example demonstrates that the symptoms and consequences of influenza infection in animals are dramatically reduced in the absence of functional TMPRSS2. The results presented in this Example therefore suggest that inhibiting TMPRSS2 activity could be an effective therapeutic strategy for treating and/or preventing influenza virus infection in human and non-human animal subjects.

Example 2

TMPRSS2 Knock-Out Mice Exhibit Reduced Viral Burden in the Lungs Compared to Wild-Type Mice Following Influenza A Virus Infection In a second set of experiments, 10 TMPRSS2-KO mice and 10 WT controls were infected with 750 PFUs of A/Puerto Rico/8/1934 H1N1 virus intranasally. The percent weight change and viral burden of the infected mice (expressed as PFUs in the lungs) were determined on day 5 post-infection. Results are shown in FIG. 5A (percent weight change) and 5B (viral burden).

Figure 5:
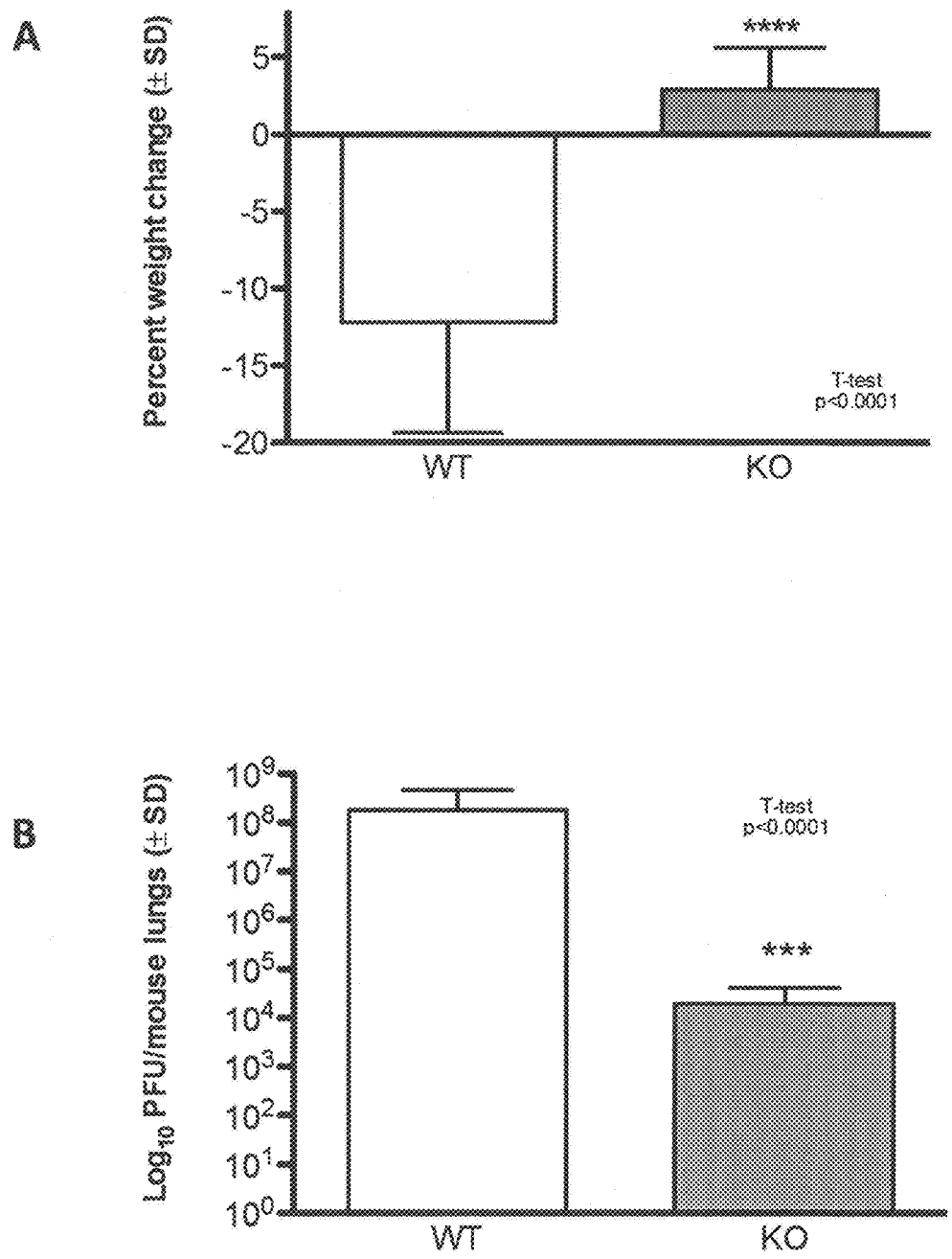
FIG. 5 shows the percent weight change (panel A) and lung viral burden (panel B) observed in wild-type mice ("WT," open bars) and TMPRSS2 knock-out mice ("KO," shaded bars) at day 5 following challenge with H1N1 influenza virus.

This set of experiments again shows that TMPRSS2-KO mice exhibit overall weight gain (~3% gain) after influenza infection, while wild-type mice exhibit significant weight loss (~12% loss) following infection (FIG. 5A). Moreover, the viral burden in the lungs of TMPRSS2-KO mice following influenza virus infection was significantly lower (~10,000-fold less) than what was observed in the lungs of infected wild-type mice (FIG. 5B). The results of this Example provide yet additional demonstration of the potential therapeutic benefits of antagonizing or inhibiting TMPRSS2 in animals infected by influenza virus.

Example 3

Whole-Lung Tissue Analysis and Sera Analysis of TMPRSS2 Knock-Out Mice Following Influenza A Virus Infection In a third set of experiments, 5 TMPRSS2-KO mice and 5 WT controls were infected with 750 PFUs of A/Puerto Rico/8/1934 H1N1 virus intranasally. Five uninfected wild-type and five uninfected TMPRSS2-KO mice were also included in the analyses. Mice were analyzed for: (1) weight change, (2) cellular changes via flow cytometry, (3) immunohistochemistry, PAS and H&E staining of whole lungs, and (4) cytokine levels in serum.

Figure 6:
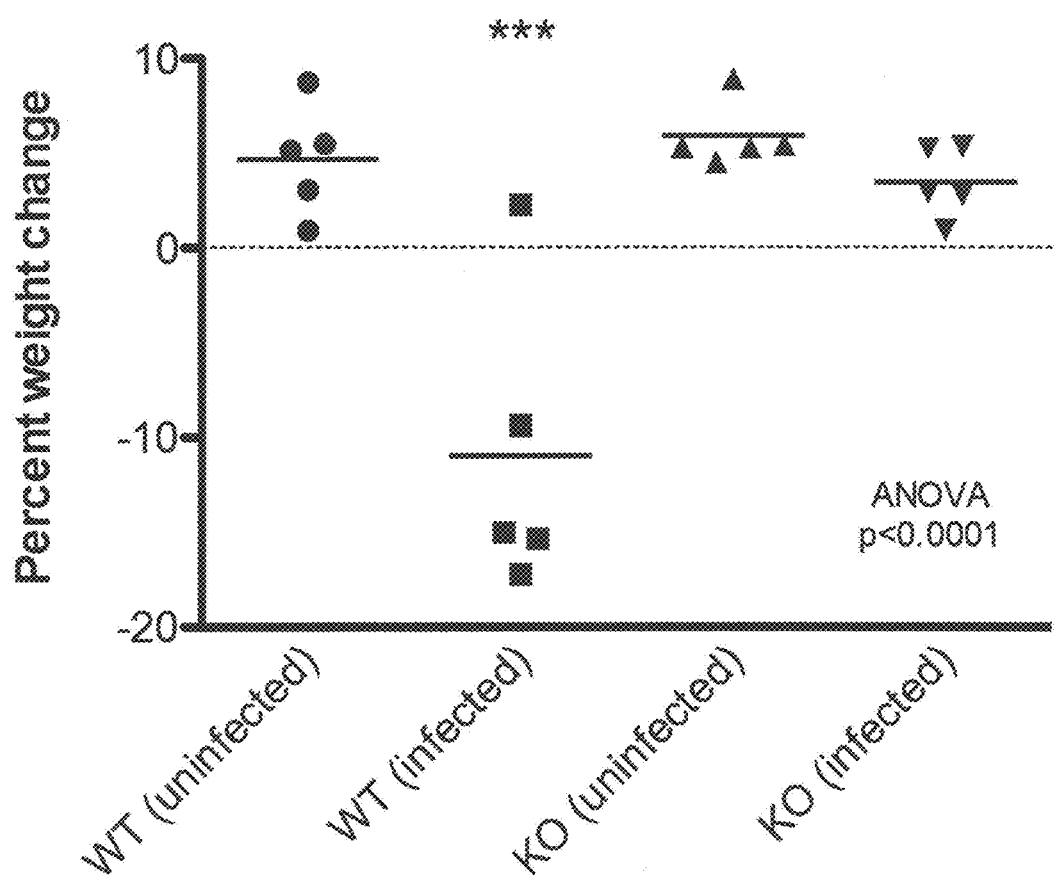
FIG. 6 shows the percent weight change observed with wild-type mice ("WT") and TMPRSS2 knock-out mice ("KO") at day 5 following challenge with H1N1 influenza virus, along with the percent weight change observed with corresponding uninfected WT and uninfected KO mice. Each symbol represents the percent weight change of an individual mouse at day 5.
Figure 7:
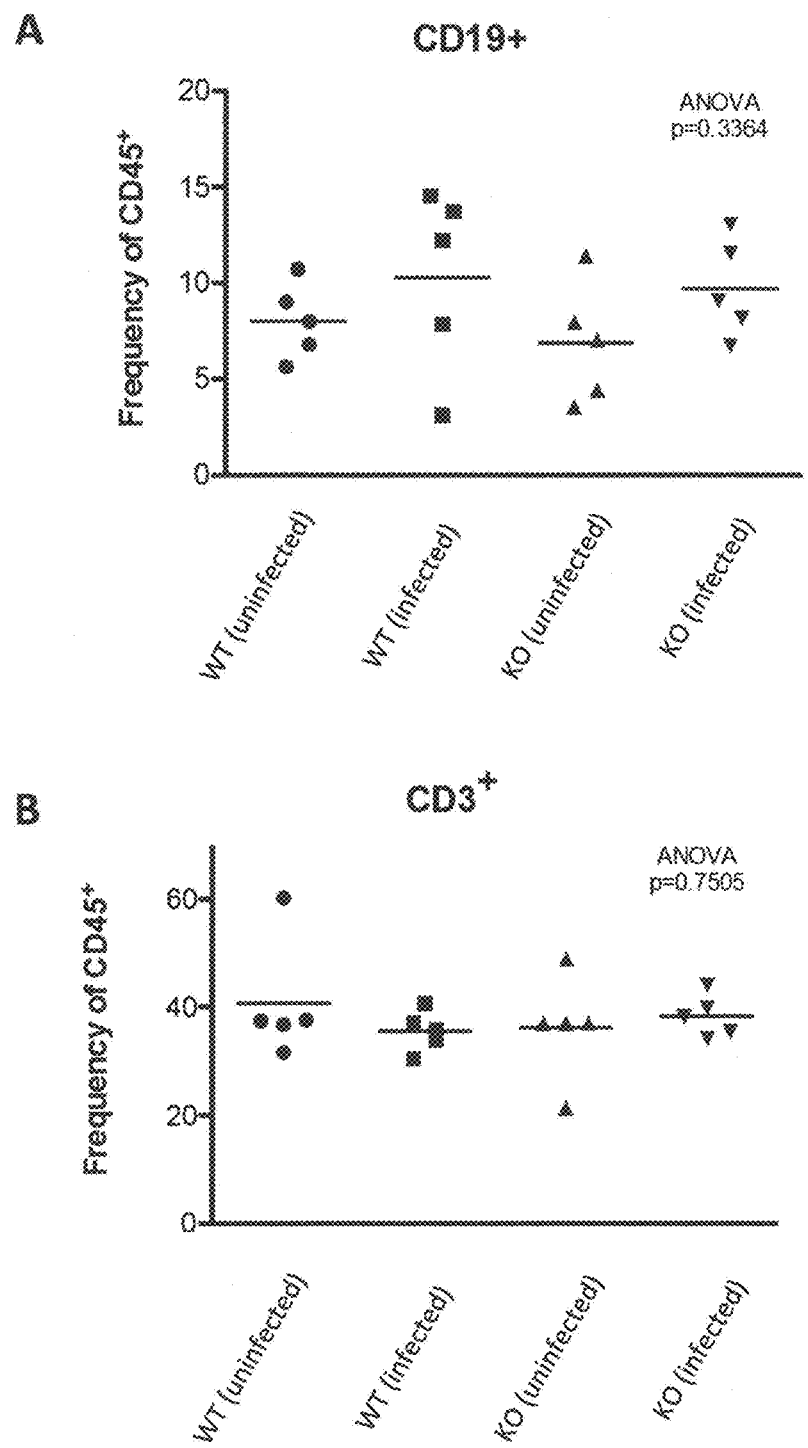
FIG. 7 shows frequency of $CD45^+$ $CD19^+$ (Panel A) and $CD45^+$ $CD3^+$ (Panel B) cells in lungs of wild-type mice ("WT") and TMPRSS2 knock-out mice ("KO") at day 5 following challenge with H1N1 influenza virus, along with the frequency of $CD45^+$ $CD19^+$ and $CD45^+$ $CD3^+$ cells in the lungs of corresponding uninfected WT and uninfected KO mice. Each symbol represents the frequency of the indicated cell type from an individual mouse at day 5.
Figure 8:
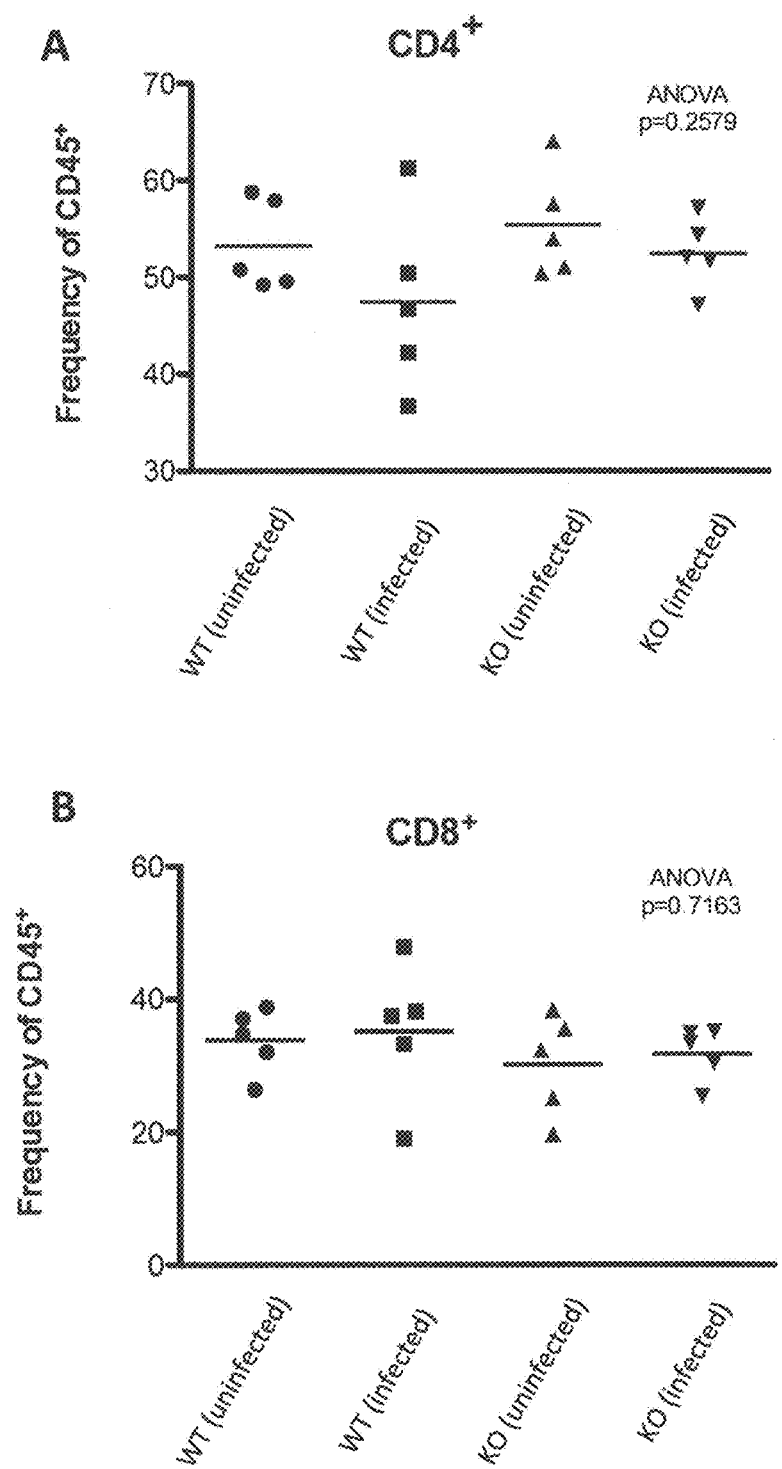
FIG. 8 shows frequency of $CD45^+$ $CD4^+$ (Panel A) and $CD45^+$ $CD8^+$ (Panel B) cells in lungs of wild-type mice ("WT") and TMPRSS2 knock-out mice ("KO") at day 5 following challenge with H1N1 influenza virus, along with the frequency of $CD45^+$ $CD4^+$ and $CD45^+$ $CD8^+$ cells in the lungs of corresponding uninfected WT and uninfected KO mice. Each symbol represents the frequency of the indicated cell type from an individual mouse at day 5.

Percent weight change observed in the mice at 5 days post-infection is depicted in FIG. 6. TMPRSS2-KO mice infected with influenza A virus ("KO infected") exhibited a 2.2-3.4% gain in starting weight, which was only slightly less than the weight gain that was observed in uninfected TMPRSS2-KO mice (5.9-6.4% gain) and uninfected WT mice (4.0-4.8% gain). Infected WT mice, on the other hand, exhibited significant weight loss (11.0-11.4% loss) by day 5 post-infection.

For the lung analyses, the following procedure was followed: First, whole lungs were harvested from each mouse. The left lung was isolated and fixed in paraformaldehyde and subjected to PAS/H&E staining for cellular damage/infiltrates. Immunohistochemical staining was used to identify infected cells. The right lung was isolated and used to generate single-cell suspensions (using Liberase™ enzymes [Roche Applied Science, Indianapolis, Ind.], DNAse and mechanical force); RBCs were lysed, cells were counted and stained for flow cytometry analysis. Cell types analyzed by this process were neutrophils, macrophages, dendritic cells, eosinophils, B cells, T cells, epithelial cells and infected cells.

Figure 9:
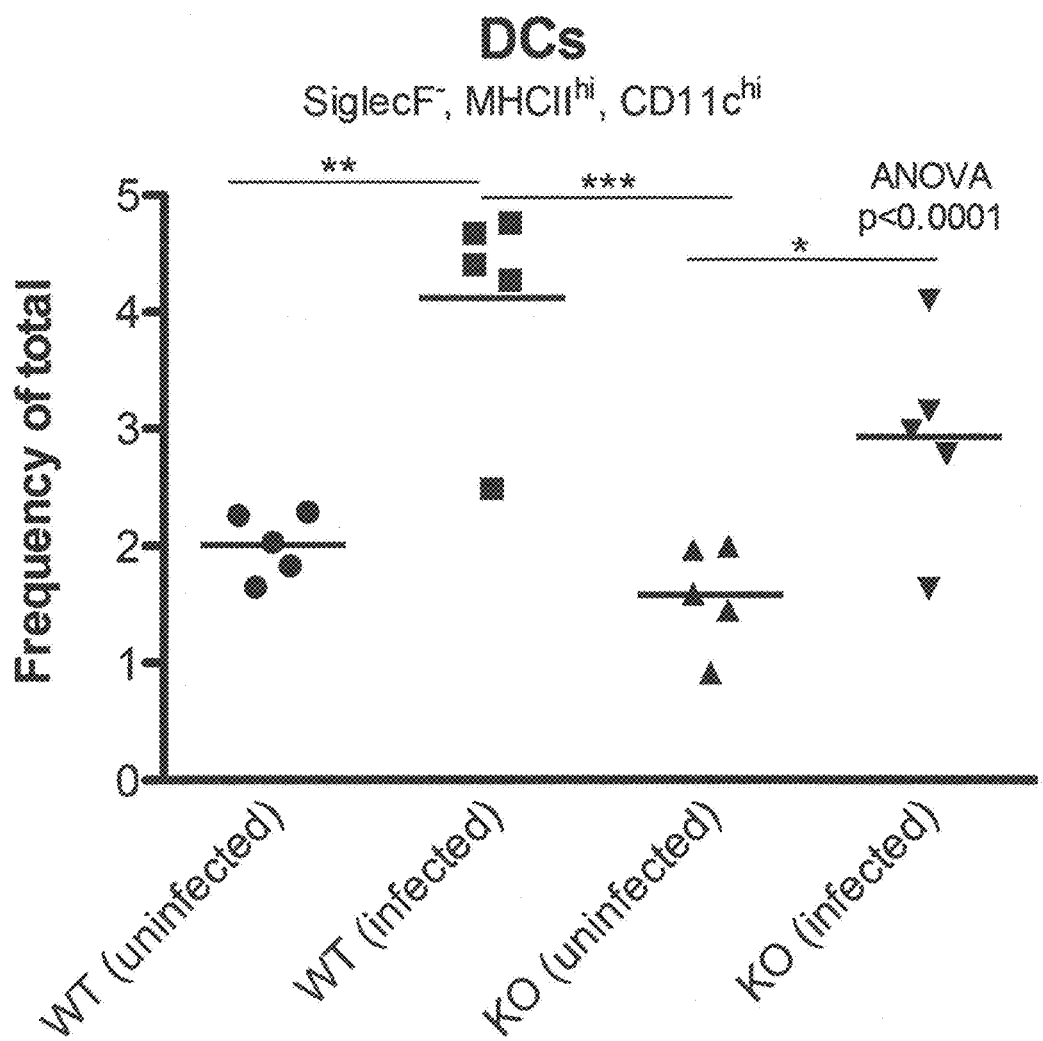
FIG. 9 shows the dendritic cell (DC) frequency in lungs of wild-type mice ("WT") and TMPRSS2 knock-out mice ("KO") at day 5 following challenge with H1N1 influenza virus, along with the DC frequency observed in the lungs of corresponding uninfected WT and uninfected KO mice. Each symbol represents the DC frequency within lung tissue from an individual mouse at day 5.
Figure 10:
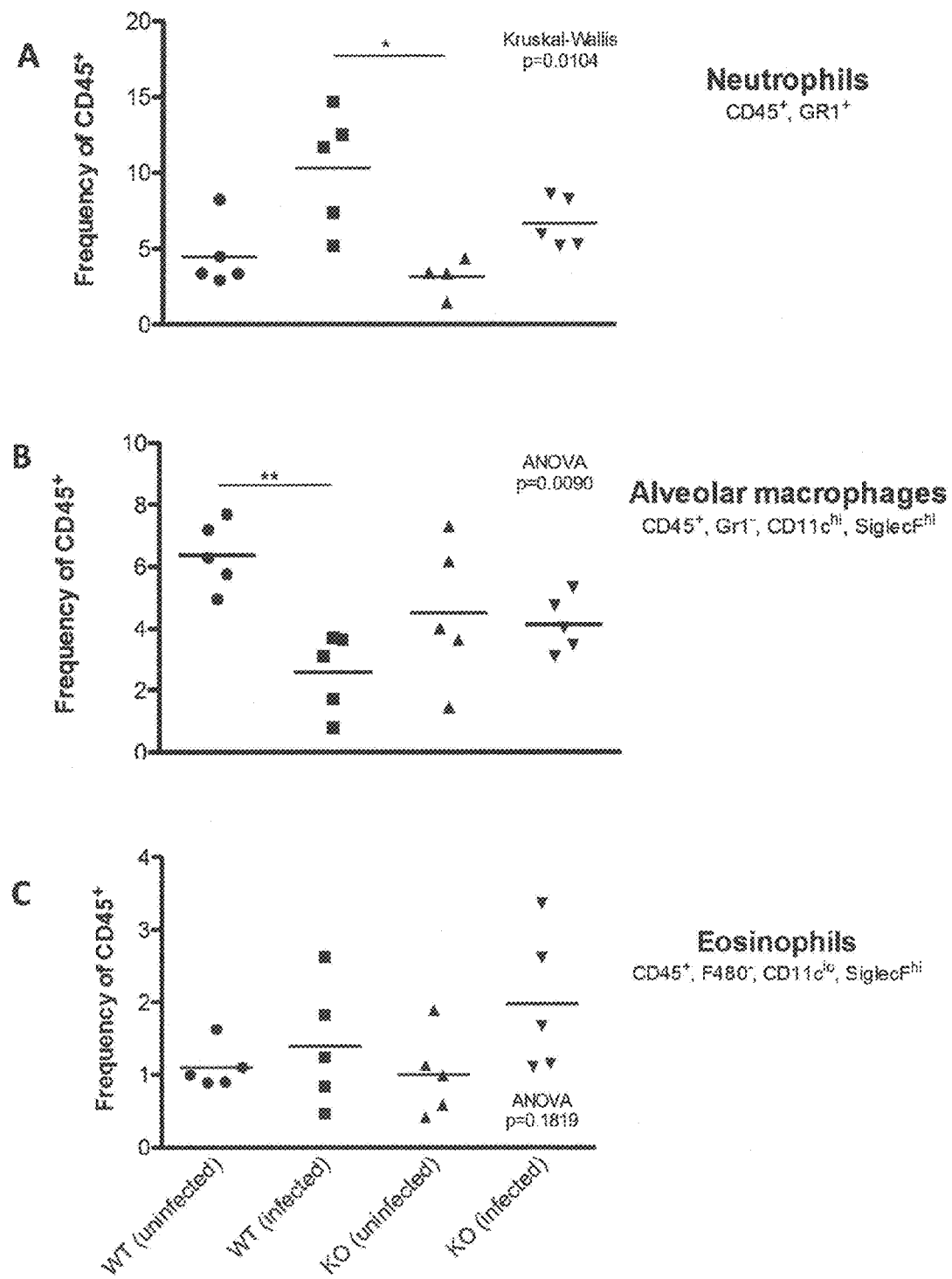
FIG. 10 shows the frequency of neutrophils (Panel A), alveolar macrophages (Panel B), and eosinophils (Panel C) in lungs of wild-type mice ("WT") and TMPRSS2 knock-out mice ("KO") at day 5 following challenge with H1N1 influenza virus, along with the frequency of neutrophils, alveolar macrophages, and eosinophils in the lungs of corresponding uninfected WT and uninfected KO mice. Each symbol represents the frequency of the indicated cell type from an individual mouse at day 5.
Figure 11:
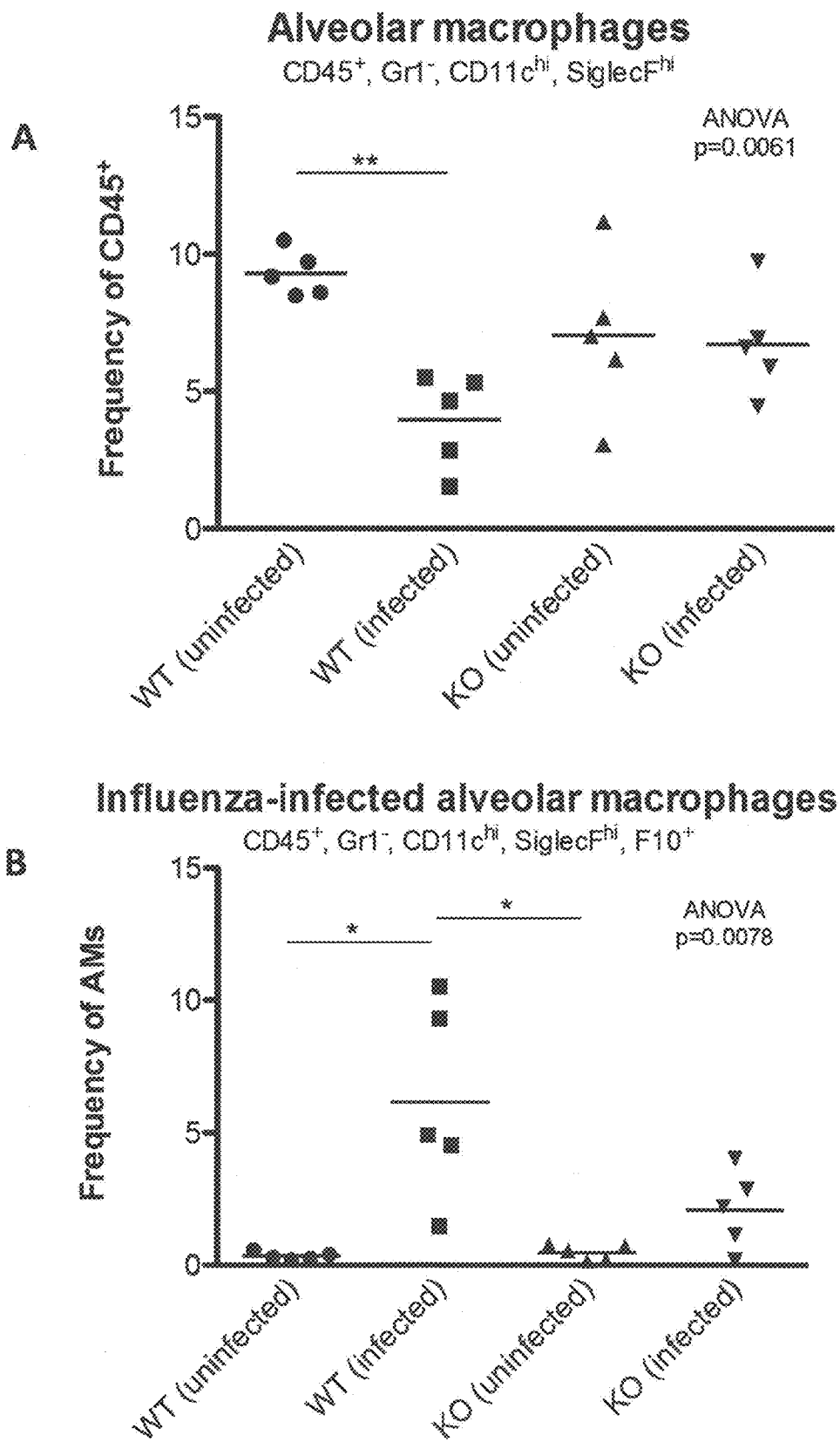
FIG. 11 shows the frequency of alveolar macrophages (panel A) and influenza-infected alveolar macrophages (panel B) in lungs of wild-type mice ("WT") and TMPRSS2 knock-out mice ("KO") at day 5 following challenge with H1N1 influenza virus, along with the frequency of alveolar macrophages and influenza-infected alveolar macrophages in the lungs of corresponding uninfected WT and uninfected KO mice. Each symbol represents the frequency of the indicated cell type from an individual mouse at day 5.
Figure 12:
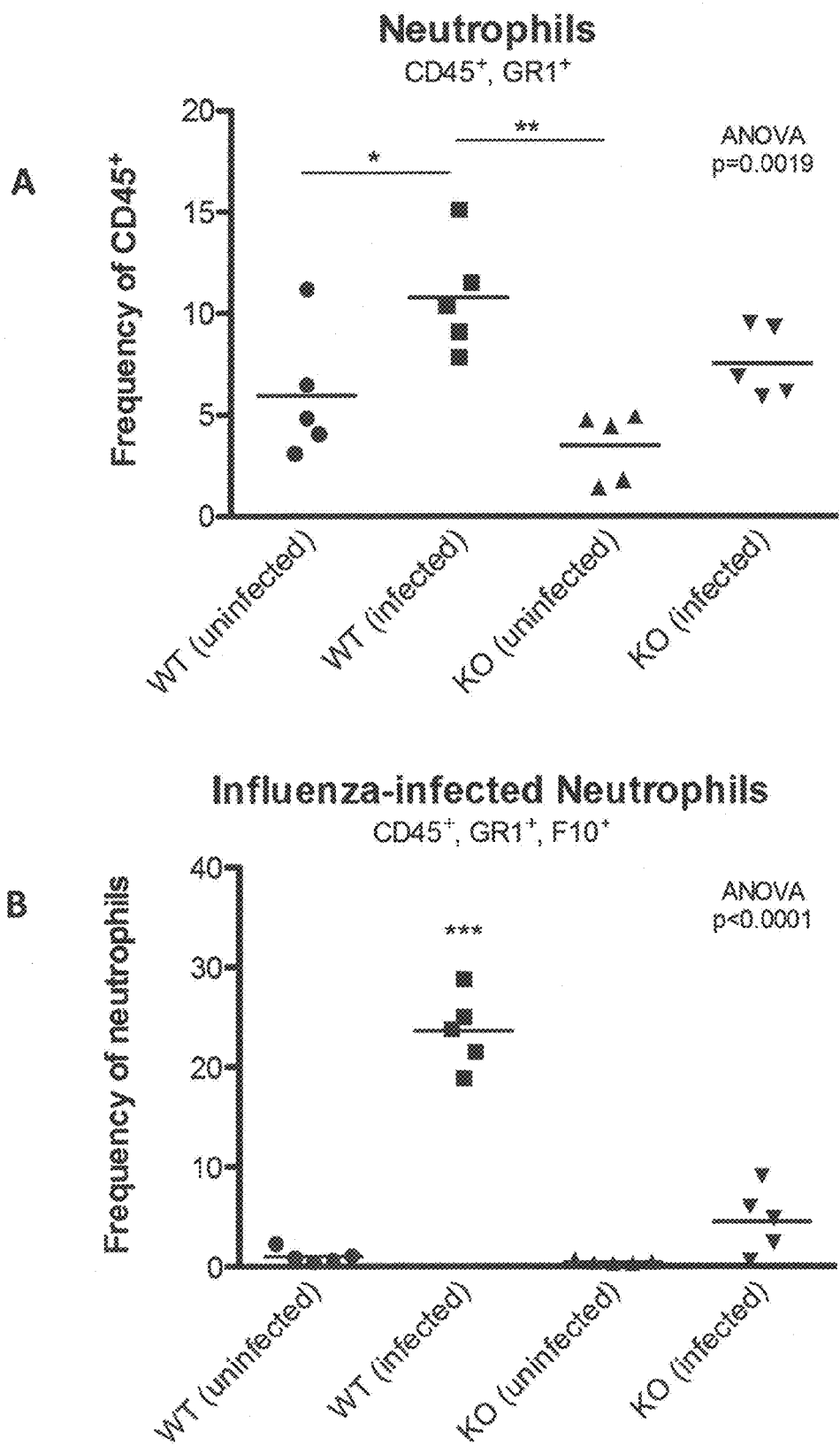
FIG. 12 shows the frequency of neutrophils (panel A) and influenza-infected neutrophils (panel B) in lungs of wild-type mice ("WT") and TMPRSS2 knock-out mice ("KO") at day 5 following challenge with H1N1 influenza virus, along with the frequency of neutrophils and influenza-infected neutrophils in the lungs of corresponding uninfected WT and uninfected KO mice. Each symbol represents the frequency of the indicated cell type from an individual mouse at day 5.

The results of the lung tissue and cell analyses are summarized as follows:

(1) No significant differences in B cells or T cells were observed among the different samples (FIGS. 7A-7B and FIGS. 8A-8B);

(2) A significant increase in the frequency of dendritic cells was observed in TMPRSS2-KO infected mice compared to TMPRSS2-KO uninfected mice; however this increase was not as pronounced as the increase that was observed in infected WT mice compared to uninfected WT mice (FIG. 9);

(3) Neither neutrophil infiltration nor alveolar macrophage levels were significantly increased in TMPRSS2-KO infected mice compared to TMPRSS2-KO uninfected mice, however WT infected mice showed significantly higher levels of neutrophils and significantly lower levels of alveolar macrophages compared to uninfected WT mice. (FIGS. 10A and 10B); eosinophil levels in lungs of infected KO mice tended to be higher than in the lungs of KO uninfected mice, but this increase was not statistically significant (FIG. 10C);

(4) No significant increases in the proportion of influenza-infected alveolar macrophages (FIG. 11B) or influenza-infected neutrophils (FIG. 12B) were observed in TMPRSS2-KO infected mice compared to TMPRSS2-KO uninfected mice; by contrast, the frequency of both influenza-infected alveolar macrophages and influenza-infected neutrophils were significantly higher in lungs of WT infected mice as compared to WT uninfected mice.

Figure 13:
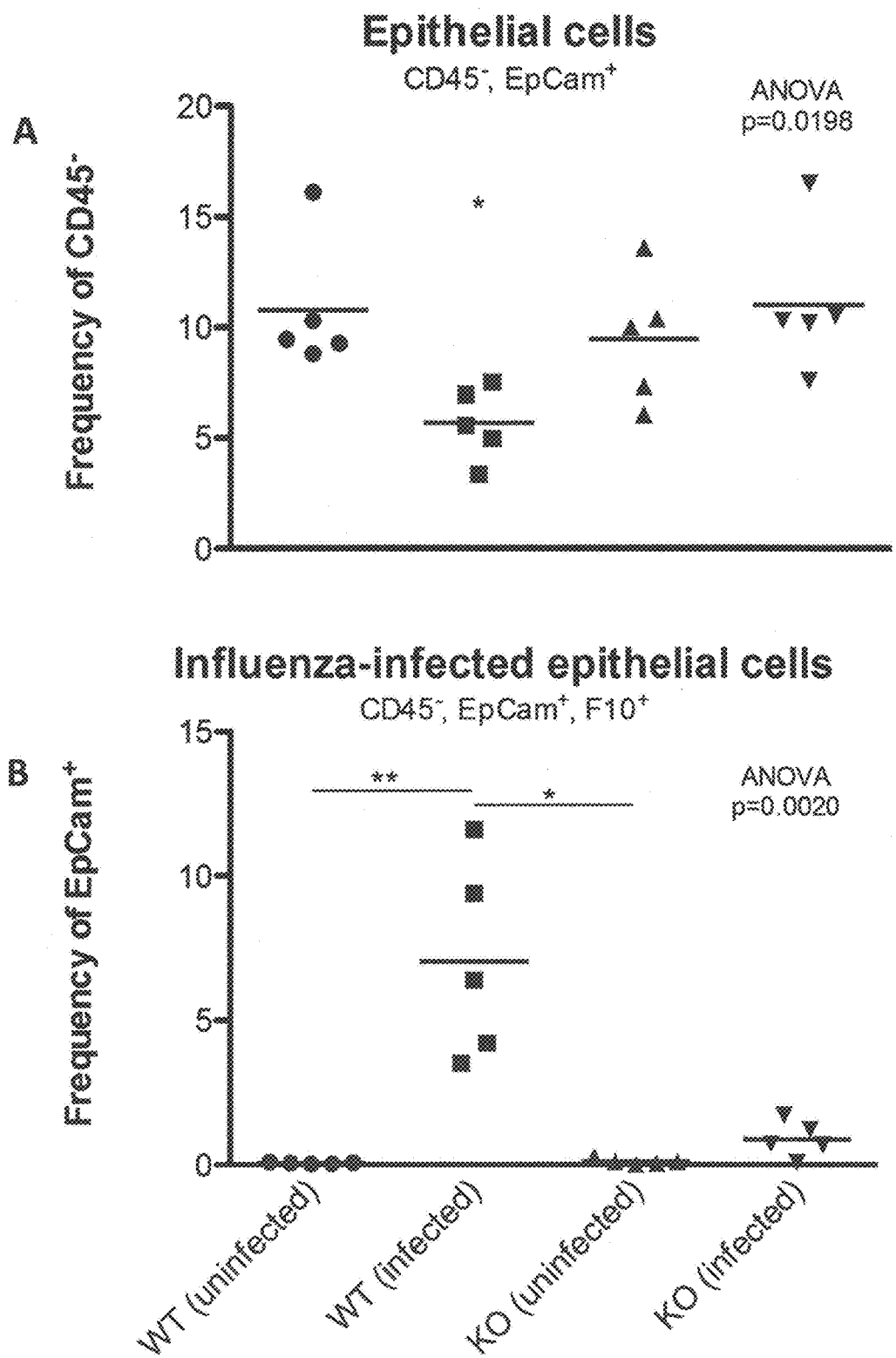
FIG. 13 shows the frequency of epithelial cells (panel A) and influenza-infected epithelial cells (panel B) in lungs of wild-type mice ("WT") and TMPRSS2 knock-out mice ("KO") at day 5 following challenge with H1N1 influenza virus, along with the frequency of epithelial cells and influenza-infected epithelial cells in the lungs of corresponding uninfected WT and uninfected KO mice. Each symbol represents the frequency of the indicated cell type from an individual mouse at day 5.
Figure 14:
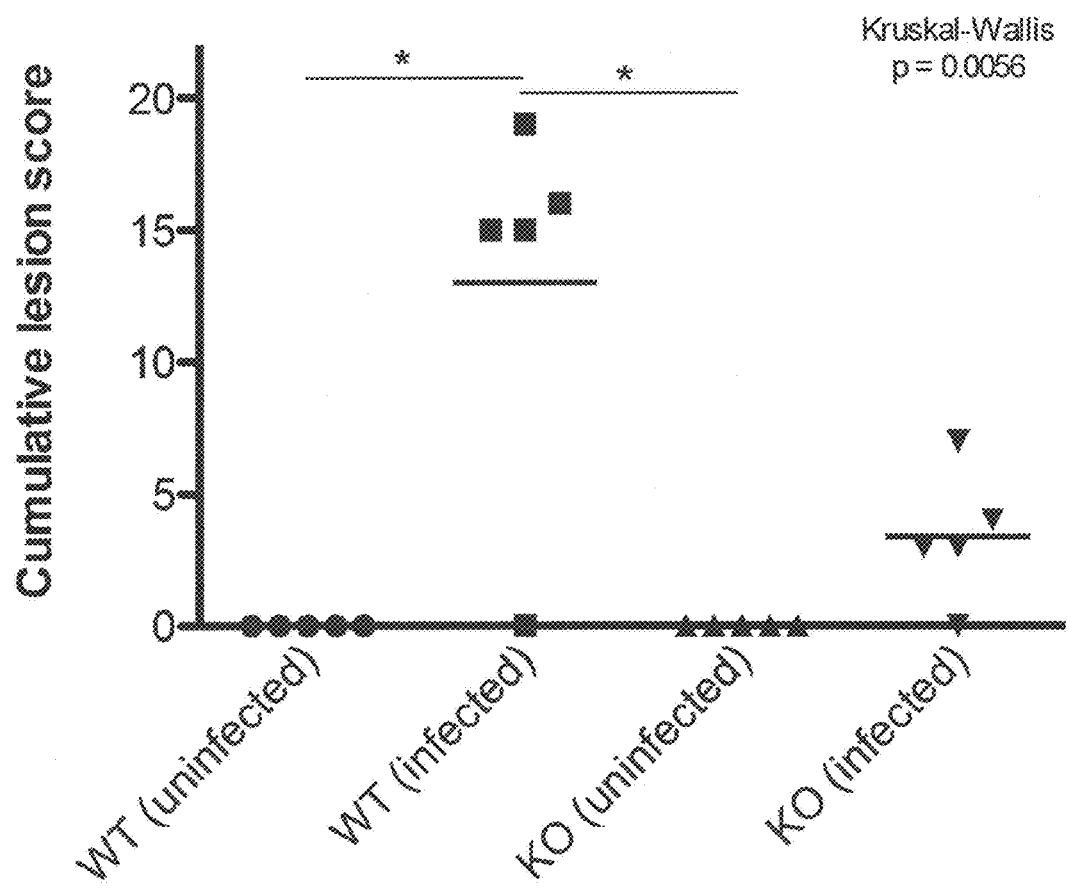
FIG. 14 shows the cumulative lesion score in lungs of wild-type mice ("WT") and TMPRSS2 knock-out mice ("KO") at day 5 following challenge with H1N1 influenza virus, along with the cumulative lesion score in lungs of corresponding uninfected WT and uninfected KO mice. Each symbol represents the cumulative lesion score in lungs from an individual mouse at day 5. Cumulative lesion score is a numerical ranking from 0 to 4 (0=not present, 1=minimal, 2=mild, 3=moderate, 4=marked) of five parameters: (1) Inflammation (bronchial and bronchiolar)=presence of inflammatory cells (neutrophils, lymphocytes, monocytes); loss (necrosis) of epithelial lining with accumulation of intraluminal cell debris; (2) Inflammation (alveolar)=alveolar lining loss, pneumocyte II hyperplasia, neutrophil and histiocytic inflammatory cells, fibrin, hemorrhage and/or cell debris deposition; (3) Infiltrate (perivascular)=mixed cellular infiltrate (lymphocytes and neutrophils), associated with endothelial reactivity, multilocal inflammatory cell margination and occasional minimal cell debris; (4) Exema/exudate=perivascular and intra-alveolar, associated with fibrin deposition and/or mixed cell infiltrate; and (5) IHC=observed in the bronchial epithelium, alveolar lining epithelium and/or alveolar macrophages.
Figure 15:
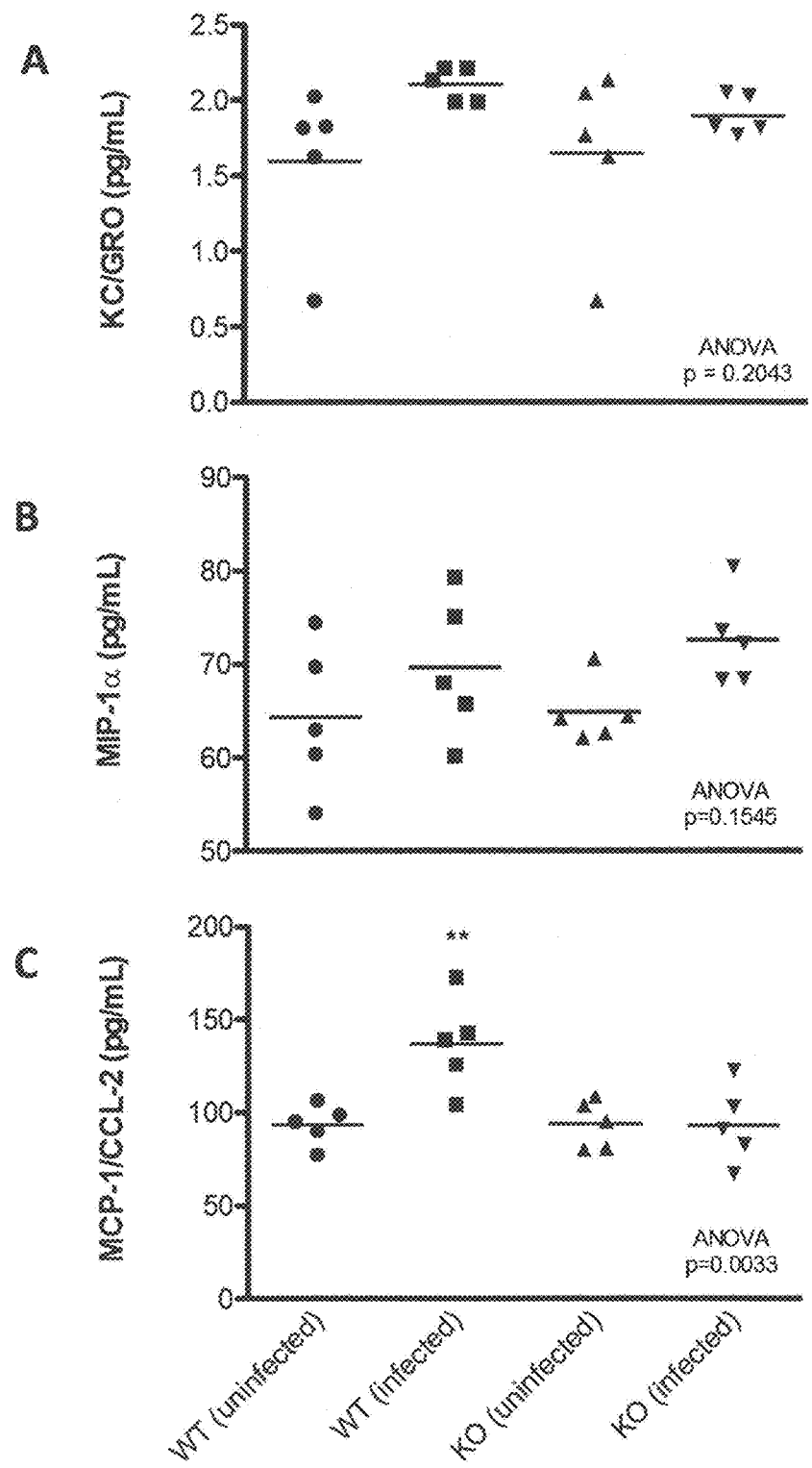
FIG. 15 shows the levels of various chemotactic cytokines (KC/GRO—Panel A; MIP-1α—Panel B; and MCP-1/CCL-2—Panel C) in serum of wild-type mice ("WT") and TMPRSS2 knock-out mice ("KO") at day 5 following challenge with H1N1 influenza virus, along with the cytokine level in serum of corresponding uninfected WT and uninfected KO mice. Each symbol represents the cytokine level (pg/mL) in serum from an individual mouse at day 5.
Figure 16:
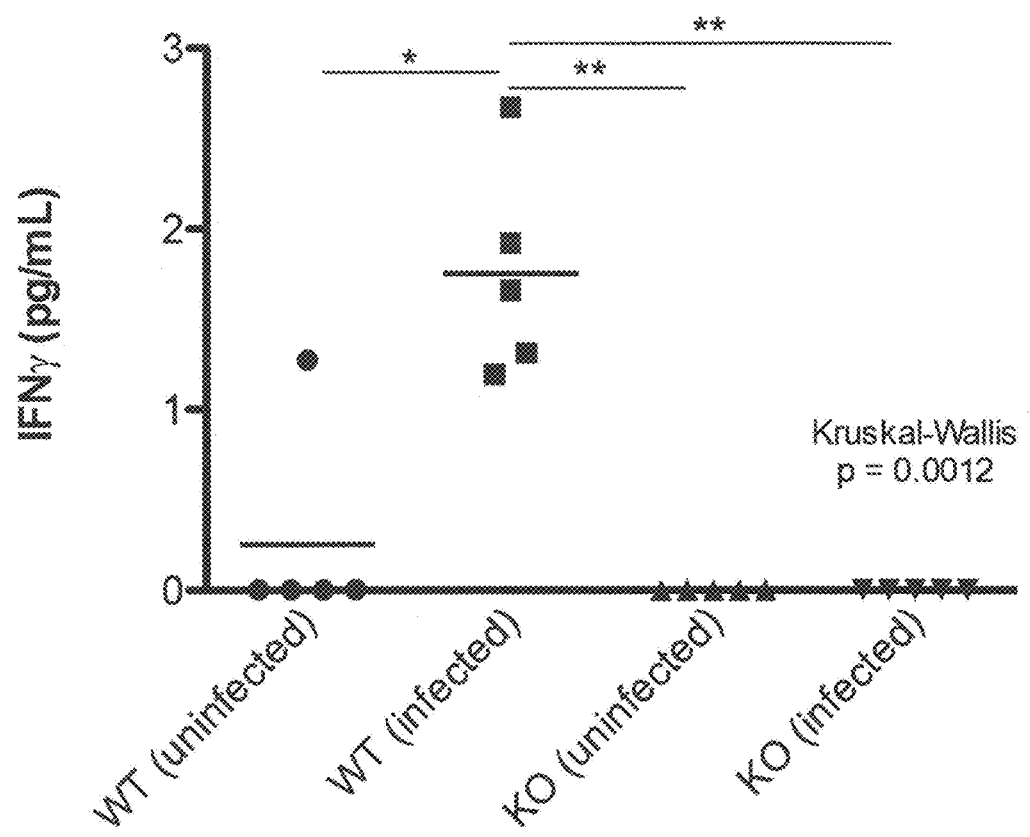
FIG. 16 shows the levels of interferon-gamma (IFNγ) in serum of wild-type mice ("WT") and TMPRSS2 knock-out mice ("KO") at day 5 following challenge with H1N1 influenza virus, along with the IFNγ level in serum of corresponding uninfected WT and uninfected KO mice. Each symbol represents the IFNγ level (pg/mL) in serum from an individual mouse at day 5.

(5) TMPRSS2-KO mice did not exhibit decreased levels of epithelial cells and there was no significant change in the proportion of influenza-positive epithelial cells compared to TMPRSS2-KO uninfected mice; by contrast, the frequency of influenza-infected epithelial cells was significantly higher in lungs of WT infected mice as compared to WT uninfected mice (FIGS. 13A-13B);

(6) Wild-type infected mice showed a significantly increased cumulative lesion score (due to inflammation, cellular infiltrate, edema and lining loss) compared to uninfected mice; the cumulative lesion score in the lungs of KO infected mice, on the other hand, tended to be only moderately higher than the cumulative lesion score in the lungs of KO uninfected mice, but this difference was not statistically significant (FIG. 14);

(7) No significant differences were observed among the different samples in terms of early cytokine levels;

(8) With regard to cytokines involved in fever and neutrophil and macrophage migration (e.g., KC/GRO, MIP-1α and MCP-1/CCL-2), no changes were observed in KC or MIP-1α levels in any of the experimental groups tested; however, a significant increase in MCP-1 was observed in WT infected mice; no statistically significant increase in MCP-1 levels was observed in KO infected mice compared to KO uninfected mice however (FIG. 15); and (9) Significantly higher levels of IFNγ were observed in samples from WT infected mice compared to samples from the other groups tested, including TMPRSS2-KO infected mice (FIG. 16).

Taken together, the results from this set of experiments confirms that TMPRSS2-KO are substantially resistant to the effects and consequences of influenza virus infection.

Example 4

Inhibition of Influenza Virus Infection In Vitro by Anti-TMPRSS Antibodies

Fully human anti-TMPRSS2 antibodies are obtained using known methods. The antibodies are tested for the ability to bind cell surface-expressed TMPRSS2. The antibodies may also be tested for the ability to bind soluble versions of TMPRSS2. Antibodies are also tested for the ability to inhibit the proteolytic activity of TMPRSS2 using standard assay formats. For example, the ability of anti-TMPRSS2 antibodies to inhibit TMPRSS2-mediated cleavage of hemagglutinin protein is assayed. Anti-TMPRSS2 antibodies with high affinity binding to TMPRSS2 and the ability to potently inhibit the proteolytic activity of TMPRSS2 are then tested in an in vitro influenza inhibition assay using human bronchial epithelial cells (Calu-3) that express TMPRSS2 (but not human airway trypsin-like protease [HAT]). It is expected that antibodies that interfere with the catalytic function of TMPRSS2 will inhibit viral propagation in this assay.

Example 5

Prevention and Treatment of Influenza Virus Infection by Anti-TMPRSS Antibodies in Animal Models Anti-TMPRSS2 antibodies are tested for their ability to prevent the effects of influenza virus infection using appropriate animal models. Antibodies that block the proteolytic activity of TMPRSS2 are administered to animals prior to experimental influenza virus infection. Control animals are treated with an isotype-matched control antibody prior to infection. It is expected that the animals that are treated with the anti-TMPRSS2 blocking antibodies will exhibit fewer and/or less severe symptoms of influenza virus infection, and/or improved viability, as compared to control treated antibodies.

Anti-TMPRSS2 antibodies are also tested for their ability to treat animals that are already infected with influenza virus. Antibodies that block the proteolytic activity of TMPRSS2 are administered to animals after experimental influenza virus infection. Control animals are treated with an isotype-matched control antibody after infection. It is expected that the animals that are treated with the anti-TMPRSS2 blocking antibodies will exhibit fewer and/or less severe symptoms of influenza virus infection, and/or improved viability, as compared to animals treated with control antibodies.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating or preventing influenza virus infection, comprising:
    injecting a mammalian subject in need thereof with a pharmaceutically effective amount of a formulation comprising a pharmaceutically acceptable carrier and a therapeutically acceptable amount of a recombinant human monoclonal antibody or antigen-binding fragment thereof that specifically binds transmembrane protease serine SI member 2 (TMPRSS2) and inhibits proteolytic enzyme activity of TMPRSS2, but does not substantially inhibit the protease activity of any other transmembrane serine protease (TTSP), and thereby decreasing influenza virus replication in the mammalian subject following exposure to influenza virus.

2. The method as claimed in claim 1, wherein the injecting is subcutaneous.

3. The method as claimed in claim 1, wherein the injecting is intravenous.

4. The method of claim 1, wherein the method results in a reduction in the accumulation of influenza-infected alveolar macrophages, influenza-infected neutrophils and/or influenza-infected epithelial cells in lungs of the mammalian subject.

* * * * *